(12) United States Patent
Streib

(10) Patent No.: US 8,215,158 B2
(45) Date of Patent: Jul. 10, 2012

(54) PROCEDURE AND DEVICE FOR DETERMINING THE VAPOR PRESSURE OF A FUEL

(75) Inventor: Martin Streib, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 364 days.

(21) Appl. No.: 12/466,113

(22) Filed: May 14, 2009

(65) Prior Publication Data

US 2010/0024528 A1 Feb. 4, 2010

(30) Foreign Application Priority Data

Jul. 31, 2008 (DE) .......................... 10 2008 040 880

(51) Int. Cl.
*G01N 7/00* (2006.01)
(52) U.S. Cl. ...................................... 73/64.45
(58) Field of Classification Search .................. 73/64.45
See application file for complete search history.

(56) References Cited

U.S. PATENT DOCUMENTS

| 3,595,082 | A * | 7/1971 | Miller, Jr. | ...................... 374/119 |
| 7,559,894 | B2 * | 7/2009 | McEowen | ...................... 600/438 |
| 2006/0287600 | A1 * | 12/2006 | McEowen | ...................... 600/481 |
| 2009/0270695 | A1 * | 10/2009 | McEowen | ...................... 600/301 |

FOREIGN PATENT DOCUMENTS

DE 102 52 225 5/2004

\* cited by examiner

*Primary Examiner* — Hezron E Williams
*Assistant Examiner* — Rodney T Frank
(74) *Attorney, Agent, or Firm* — Merchant & Gould P.C.

(57) ABSTRACT

A procedure for determining the vapor pressure of a fuel in a tank is provided, whereby the sound velocity and/or a variable representing the sound velocity are determined the in the gas-filled compartment of the tank and the vapor pressure is assumed from the sound velocity and/or from the variable representing the sound velocity at a familiar total pressure.

12 Claims, 3 Drawing Sheets

PROCEDURE AND DEVICE FOR DETERMINING THE VAPOR PRESSURE OF A FUEL

TECHNICAL FIELD

The present invention concerns a procedure and a device for determining the vapor pressure of a fuel in a tank as well as a computer program and a computer program product for implementing the procedure.

BACKGROUND

For various applications at the control of combustion engines, in particular at the control of combustion engines for motor vehicles, it is required to determine the vapor pressure of the fuel in the fuel tank. By knowing the vapor pressure of the fuel statements for example can be made about the volatility of the fuel and therefore about the features of the actually used fuel. Traditional procedures usually use a pressure sensor in the fuel tank for determining the vapor pressure of the fuel, whereby the partial pressure of the gaseous fuel vapors can be assumed by measuring the pressure.

But such pressure measurements do not always provide satisfactory results. In particular only the total pressure can be measured. Reliable statements about the partial pressure of the fuel vapors are not possible without further ado. The German patent application DE 102 52 225 A1 suggests therefore for example to determine the vapor pressure of the fuel over the temperature dependency of a parameter of the tank ventilation system, which indirectly correlates with the internal pressure that exists in the fuel tank system. But several mistakes can occur at this indirect determination of the vapor pressure, so that this procedure is also not always satisfactory.

In contrast the invention sets oneself the task to enable a reliable determination of the vapor pressure of the fuel by simple means. Thereby the disadvantages of the state of the art shall be avoided. By the determination of the vapor pressure of the fuel for example statements about the fuel volatility and therefore statements about the features of the actually used fuel shall be made, which can be used for an improvement of for example the transmission compensation, the start enhancement and such alike.

SUMMARY

This task is solved by a procedure and a device as they are described in the independent claims. Preferred embodiments of this procedure and the device are stated in the dependant claims.

The procedure according to the invention serves the determination of the vapor pressure of a fuel in a tank. Thereby the sound velocity and/or a variable that represents the sound velocity are determined in the gas-filled compartment of the tank. The gas-filled compartment is the part of the tank, which comprises the gas phase of the fuel. The vapor pressure of the fuel is assumed from the sound velocity and/or the variable representing the sound velocity at a familiar total pressure, in particular the pressure in the tank. By determining the vapor pressure of the fuel conclusions about the fuel volatility can be made. The knowledge of the fuel volatility can for example be used at the engine control for example for improving the transmission compensation, the start enhancement and such alike. By knowing the fuel volatility moreover statements about the actually used fuel quality or -type can be made. The knowledge of the actually used fuel type is essential for a number of control steps in the motor vehicle for operating the combustion engine, in order to enable an optimal operation. Usually a typically average fuel type is assumed often in the vehicle control, so that the different control steps do not allow an optimal operation of the combustion engine. Other approaches use relatively vague indications for the diagnosis of the fuel type in order to enable at least partially an adjustment of the control steps at the actually used fuel. An example for such indications is the external temperature. Thereby the use of winter- or summer fuel can be assumed. The vapor pressure of the fuel in the tank that can be determined according to the invention allows on the other hand an exact differentiation of fuel types by their different volatility and enables therefore an accurate diagnosis of the actually used fuel type. Thereby an optimal adjustment of the engine control is enabled.

In a preferred embodiment of the procedure according to the invention the density of the gaseous phase in the tank is concluded from the sound velocity and/or the variable representing the sound velocity. The relation between fuel vapor and air is concluded from the density and the vapor pressure at familiar total pressure in the tank system is concluded from the relation between fuel vapor and air.

As it is known air and gaseous fuel have different densities at the same temperature. The density on the other hand influences the sound velocity in gases according to the formula:

$$cs = \sqrt{\frac{kappa \times p}{rho}}$$

Thereby
cs is the sound velocity,
kappa is the poly-tropic exponent of the gas,
p is the pressure and
rho is the density.

The pressure in the tank system is measured by a corresponding sensor technology or can be assumed from suitable pressure models. The poly-tropic exponent kappa of air is circa 1.4. The poly-tropic exponent kappa for typical fuel vapors is circa 1.2 to 1.3. Due to the low difference an average value of the poly-tropic exponents kappa of air and of fuel vapors is preferably assumed for the procedure according to the invention. This averaging enables a calculation of the density of the gas mixture in a tank container according to the above described formula.

Alternatively or additionally kappa can be determined recursively. Therefore a first value for the density is determined with the aid of the measurement of the sound velocity with an assumed value for kappa, in particular a value between 1.2 and 1.4. Depending on this value a new approximate value is determined for kappa. Thereby kappa is closer to 1.2 the bigger the calculated value for the density is. The lower the calculated density is the closer kappa is located around 1.4. With the new value for kappa a new value for the density can be determined with the aid of the measured sound velocity or the measured variable representing the sound velocity, which can create a further for the described recursion.

According to the invention the relation between fuel vapor and air can be assumed from the density of the gas mixture and from this relation the vapor pressure of the fuel can be concluded. The higher the density the greater the relation of the fuel vapor to air in the tank or in the gas phase of the tank. From this relation the partial pressure of the fuel vapor can be assumed. That can for example take place with the aid of a characteristic line. The function that is based on such a characteristic line can for example be stored as mathematical function in a control unit. With the aid of this function the partial pressure of the fuel vapor can be determined arithmetically.

In a particularly preferred embodiment of the procedure according to the invention several vapor pressure curves are stored as functions of the temperature for different fuels. When knowing the actual temperature and the vapor pressure or partial pressure of the fuel that has been determined according to the invention the vapor pressure curve can be used that is the closest to the actually used fuel and thereof the actually used fuel type can be concluded. Preferably the different stored vapor curves represent the partial pressure of fuels, which differ from each other by its volatility or fugacity.

The invention furthermore comprises a procedure for determining a fuel type and/or a fuel volatility, whereby the vapor pressure can be concluded from the sound velocity and/or from the variable representing the sound velocity in the gas-filled compartment of a fuel tank at a familiar total pressure and under consideration of the courses of the vapor pressure as function of the temperature for at least two fuel types with different volatility at a familiar temperature the fuel type that is present in the tank and/or fuel volatility is assumed. With regard to further features of the procedure according to the invention for determining the fuel type and/or fuel volatility it is referred to the above description.

In a preferred embodiment of the procedure according to the invention the sound velocity is determined by a duration measurement of at least one sound event in the gas phase of the tank by inducing or creating at least one sound event at at least one sound source in the tank and by detecting it by at least one sound detector in the tank.

In another embodiment of the procedure according to the invention the measurement of the sound velocity takes place by a resonance measurement of at least one sound event in the gas phase of the tank. Therefore a sound resonator with sound source, sound detector and preferably reflector is provided in the tank system. The sound source creates sound with a variable frequency. With the aid of the detector it is determined at which frequency a resonance occurs. From this frequency the sound velocity can be determined.

The invention furthermore comprises a device for determining he vapor pressure of a fuel in a tank. The device according to the invention comprises a tank for fuel, which provides means for detecting the sound velocity and/or variable representing the sound velocity in the gas-filled compartment of the tank. Preferably means are provided for the duration measurement of at least one sound event. Preferably at least one device is therefore provided for creating a sound and at least one device for detecting the sound. In another preferred embodiment means are arranged in the gas phase of the tank for the resonance measurement of at least on sound event. Preferably a sound resonator is therefore provided with at least one sound source and at least one sound detector. Preferably the sound resonator comprises furthermore at least one reflector. With regard to further features of the device according to the invention it is referred to the above description.

The invention comprises furthermore a computer program, which carries out the described steps of the procedure, if it runs on an arithmetic unit, for example a control unit of a combustion engine. Finally the invention comprises a computer program product with a program code, which is stored on a machine-readable device, for implementing the described procedure, if the program is carried out on a computer or a control unit. The computer programs or computer program products are used particularly advantageously for determining the vapor pressure of a fuel in a tank and/or determining the fuel type and/or fuel volatility in corresponding control units of motor vehicles.

Further advantages and characteristics of the invention arise from the subsequent description of the figures together with the embodiments. Therefore the different characteristics can be realized alone or in combination with each other.

DETAILED DESCRIPTION

Figure 1:
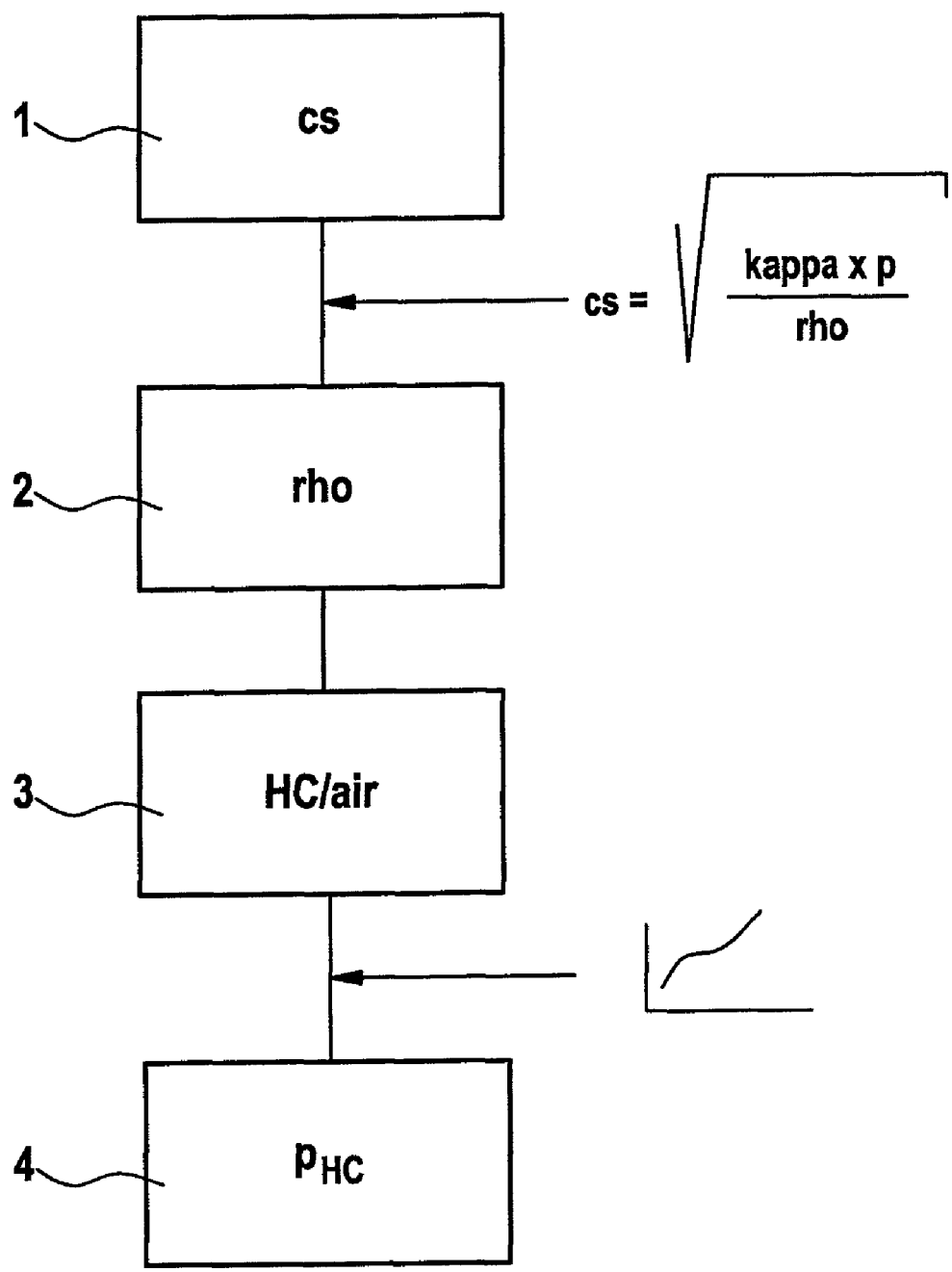
FIG. 1 shows schematically a block diagram for illustrating a preferred embodiment of the procedure according to the invention.

According to the block diagram shown in FIG. 1 the sound velocity (cs) and/or a variable representing the sound variable are first measured in step 1 in the gas-filled compartment of the fuel tank. In step 2 the density (rho) in the gas-filled compartment of the tank is calculated with the aid of the formula $$cs = \sqrt{\frac{kappa \times p}{rho}}$$

from the sound velocity or the variable representing the sound velocity. Thereby cs is the sound velocity,
kappa is the poly-tropic exponent of the gas,
p is the pressure and
rho is the density.

From the calculated density the relation of fuel (HC) to the air (air) is determined in step 3. The relation of fuel to air is thereby greater the higher the calculated density is. The partial pressure of the fuel vapor (pHC) is for example determined with the aid of a characteristic line in step 4. Particularly advantageously the fuel type that is present in the tank is concluded under consideration of courses of the vapor pressure as a function of the temperature for at least two fuel types with a different volatility at a familiar temperature.

Accordingly the procedure according to the invention can be used for determining the fuel type and/or fuel volatility.

Figure 2:
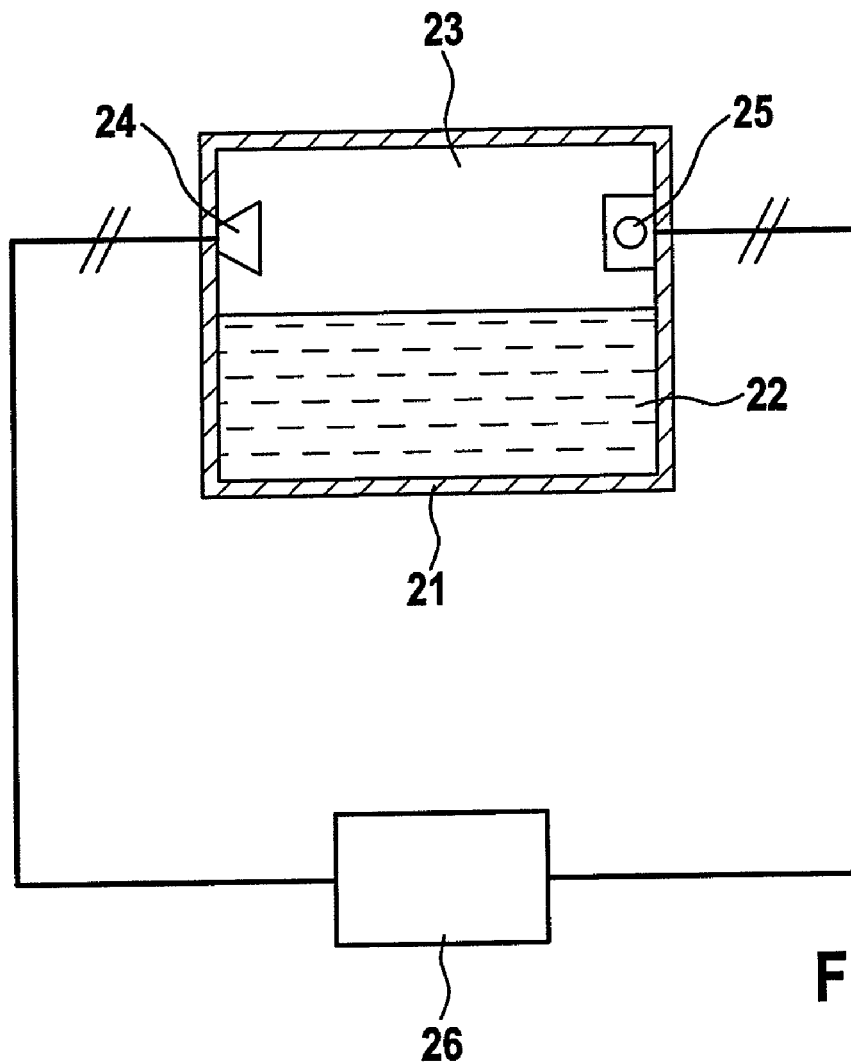
FIG. 2 shows schematically an illustration of a fuel tank with a suitable sensor technology for implementing the procedure according to the invention.

Preferably the measurement of the sound velocity and/or of the variable representing the sound velocity takes place by a duration measurement of at least one sound event in the tank, whereby preferably at least one sound event at at least one sound source in the tank is induced and detected by at least on sound detector. Therefore at least one sound source and at least one sound detector are provided in the gas-filled compartment of the tank. Sound source and sound detector are correspondingly controlled and evaluated, so that from the duration of the sound the sound velocity and/or a variable representing the sound velocity can be detected. FIG. 2 shows a fuel tank 21 with a suitable sensor technology for implementing the procedure according to the invention. The fuel tank 21 comprises the liquid phase 22 and the gas phase 23 of the fuel. In the area of the gas phase 23 as sound source 24 and a sound detector 25 are arranged, which for example can be provided at opposite sides of the fuel tank 21. For measuring the sound velocity the sound source 24 is controlled by a suitable control unit 26. The duration of the sound until the receiving by the sound detector 25 is measured. The measured sound velocity is evaluated in the control unit 26 according to the invention's procedure.

Figure 3:
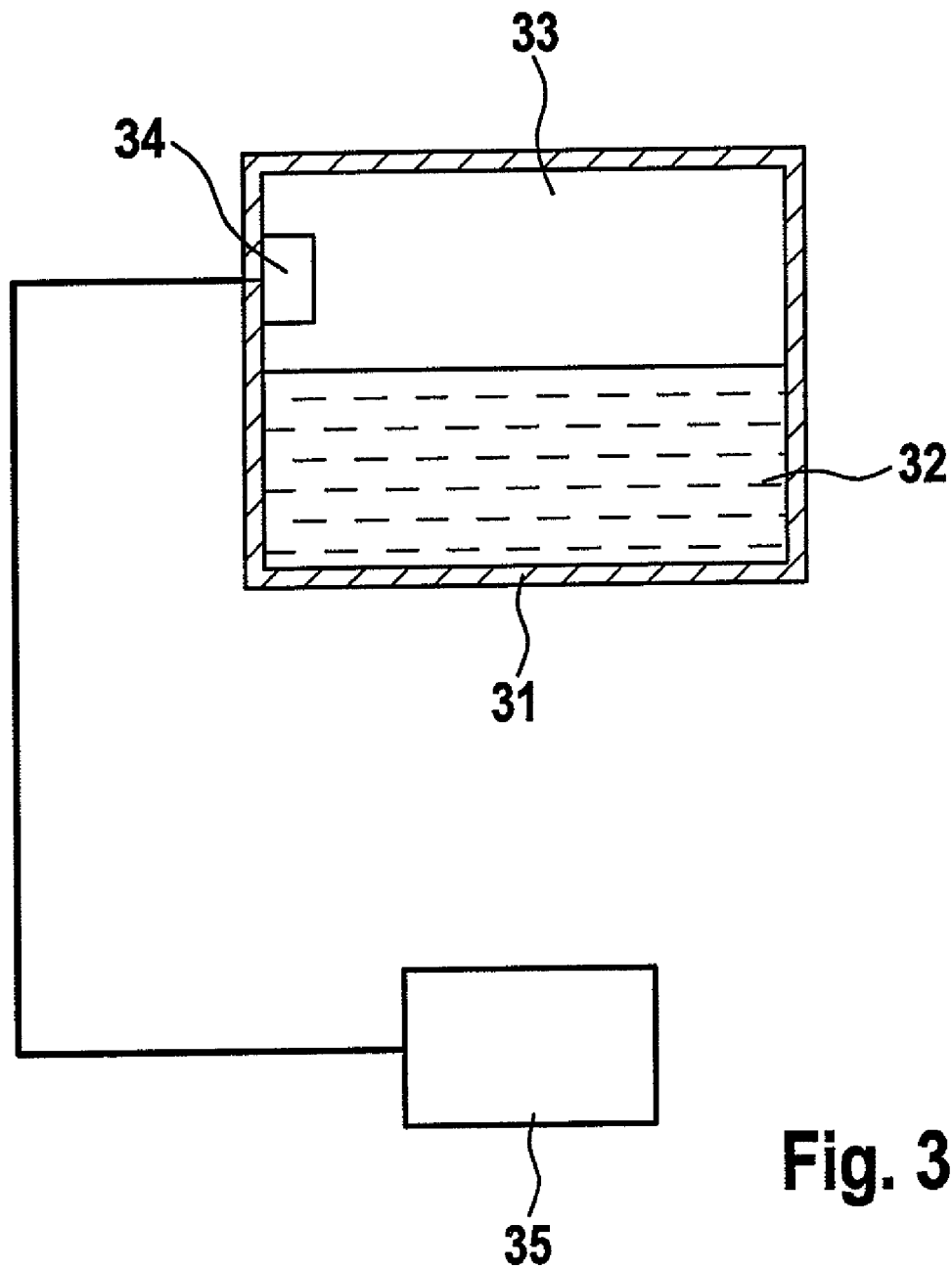
FIG. 3 shows schematically an illustration of a further embodiment of a fuel tank with a suitable sensor technology for implementing the procedure according to the invention.

In a further embodiment of the procedure according to the invention the measurement of the sound velocity and/or the measurement of a variable representing the sound velocity takes place by a resonance measurement. At an acoustic wave the sound velocity is the product of the frequency and wave length. If one builds an acoustic resonator for example into the tank, the wave lengths, at which a resonance occurs, is determined by the geometry of the resonator. If one goes now through the frequencies with a sound generator and detects the frequency, at which resonance occurs, the sound velocity can be determined from this frequency and the wave length. Thus at least one sound event is created in the tank with a variable frequency and the frequency is determined by at least one sound detector, at which the resonance occurs. From this frequency the sound velocity and/or the variable representing the sound velocity is concluded. FIG. 3 shows a fuel tank 31 with a liquid phase 32 and a gas phase 33 of the fuel, which is suitable for implementing this embodiment o the procedure according to the invention. A sound resonator 34 is arranged in the tank 31 in the area of the gas phase of the fuel 33. The sound resonator 34 comprises a sound source, a sound detector and preferably a reflector. The sound source in the sound resonator 34 is provided for creating sound with variable frequency. With the aid of the sound detector within the sound resonator 34 the frequency is determined, at which resonance occurs, so that from this frequency the sound velocity can be determined. For controlling and processing the corresponding signals a control unit 35 is provided.

The invention claimed is:

1. A method of determining a vapor pressure of a fuel in a tank, the method comprising the steps of:
   determining in a control unit at least one of a sound velocity and a variable representing the sound velocity of a sound transmitted from a sound source through a gas-filled compartment of the fuel tank to a sound detector;
   determining in the control unit the vapor pressure of the fuel in the tank based on the determined at least one of the sound velocity and the variable representing the sound velocity at a known total pressure.

2. The method of claim 1, further comprising:
   determining a density from the at least one of a sound velocity and a variable representing the sound velocity;
   determining a relation between a fuel vapor and air from the density; and
   determining the vapor pressure of the fuel from the relation of the fuel vapor and air can.

3. The method of claim 1, further comprising determining a poly-tropic exponent of the gas mixture in the gas-filled compartment recursively or by a poly-tropic exponent of kappa of the fuel vapor and a poly-tropic exponent of air.

4. The method of claim 1, further comprising determining a fuel type in the tank under consideration of courses of the vapor pressure as a function of temperature for at least two fuel types with a different volatility at a familiar temperature.

5. The method of claim 1, further comprising determining the at least one of a sound velocity and a variable representing the sound velocity from a duration measurement of at least one sound event in the gas phase of the tank, wherein at least one sound event is created by at least one sound source in the tank and detected by at least one sound detector.

6. The method of claim 1, further comprising determining the at least one of a sound velocity and a variable representing the sound velocity from a resonance frequency during a resonance measurement of at least one sound event in the gas phase of the tank, wherein the at least one sound event is created by a sound resonator with a variable frequency.

7. A method of determining at least one of a fuel type and a fuel volatility of a fuel in a tank, the method comprising the steps of:
   determining in a control unit at least one of a sound velocity and a variable representing the sound velocity of a sound transmitted from a sound source through a gas-filled compartment of the fuel tank to a sound detector;
   determining in a control unit a vapor pressure of the fuel in the tank from the determined at least one of a sound velocity and a variable representing the sound velocity in the gas-filled compartment of the tank at a known total pressure; and
   determining in a control unit the at least one of the fuel type and the fuel volatility based on courses of the determined vapor pressure as a function of temperature for at least two fuel types with a different volatility at a known temperature.

8. The method of claim 7, further comprising:
   determining a density from the at least one of a sound velocity and a variable representing the sound velocity;
   determining a relation between a fuel vapor and air from the density; and
   determining the vapor pressure of the fuel from the relation of the fuel vapor and air.

9. A device configured to determine a vapor pressure of a fuel in a tank, comprising:
   a sound source configured to transmit a sound in a gas-filled compartment of the fuel tank;
   a sound detector configured to receive the sound transmitted by the sound source; and
   a control unit configured to determine at least one of a sound velocity and a variable representing the sound velocity provided in the gas-filled compartment of the tank and to determine a vapor pressure of the fuel in the tank based on the determined at least one of the sound velocity and the variable representing the sound velocity at a known total pressure.

10. The device of claim 9, wherein the control unit is configure to measure resonance of at least one sound event including at least one sound resonator with at least one sound source, at least one sound detector, and at least one reflector.

11. A computer-implemented method for determining a vapor pressure of a fuel in a tank, the computer-implemented method comprising the steps of:
   determining in a control unit at least one of a sound velocity and a variable representing the sound velocity of a sound transmitted from a sound source through a gas-filled compartment of the fuel tank to a sound detector;
   determining in the control unit the vapor pressure of the fuel in the tank based on the determined at least one of the sound velocity and the variable representing the sound velocity at a known total pressure.

12. A computer program product with a program code stored on a machine-readable device and executed on a computer or a control unit, for determining a vapor pressure of a fuel in a tank, the program code including instructions for:
   determining in a control unit at least one of a sound velocity and a variable representing the sound velocity of a sound transmitted from a sound source through a gas-filled compartment of the fuel tank to a sound detector;
   determining in the control unit the vapor pressure of the fuel in the tank based on the determined at least one of the sound velocity and the variable representing the sound velocity at a known total pressure.

* * * * *